United States Patent
Akashi et al.

(10) Patent No.: US 9,896,451 B2
(45) Date of Patent: Feb. 20, 2018

(54) METHOD FOR PRODUCING ENDO-9-AZABICYCLO[3.3.1]NONAN-3-OL DERIVATIVE

(71) Applicant: Nippon Soda Co., Ltd., Tokyo (JP)

(72) Inventors: Masaya Akashi, Joetsu (JP); Tsutomu Inoue, Chigasaki (JP); Hirohito Oooka, Hadano (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/913,736

(22) PCT Filed: Aug. 14, 2014

(86) PCT No.: PCT/JP2014/071434
§ 371 (c)(1),
(2) Date: Feb. 23, 2016

(87) PCT Pub. No.: WO2015/033753
PCT Pub. Date: Mar. 12, 2015

(65) Prior Publication Data
US 2016/0200726 A1 Jul. 14, 2016

(30) Foreign Application Priority Data

Sep. 6, 2013 (JP) .................. 2013-185712

(51) Int. Cl.
*C07D 471/08* (2006.01)
*C07B 53/00* (2006.01)
*C07D 451/14* (2006.01)
*B01J 31/18* (2006.01)
*B01J 31/24* (2006.01)

(52) U.S. Cl.
CPC ........ *C07D 471/08* (2013.01); *B01J 31/1805* (2013.01); *B01J 31/189* (2013.01); *B01J 31/1815* (2013.01); *B01J 31/24* (2013.01); *B01J 31/2409* (2013.01); *B01J 31/2447* (2013.01); *C07B 53/00* (2013.01); *C07D 451/14* (2013.01); *B01J 2231/643* (2013.01); *B01J 2531/821* (2013.01)

(58) Field of Classification Search
CPC .................................................. C07D 471/08
See application file for complete search history.

(56) References Cited

U.S. PATENT DOCUMENTS

| 6,498,159 | B1 | 12/2002 | Watanabe et al. |
| 7,638,628 | B2 | 12/2009 | Baratta et al. |
| 8,436,181 | B2 | 5/2013 | Ohkuma et al. |
| 9,255,049 | B2 | 2/2016 | Hori et al. |
| 2008/0249308 | A1 | 10/2008 | Baratta et al. |
| 2010/0174081 | A1 | 7/2010 | Ohkuma et al. |
| 2012/0010417 | A1 | 1/2012 | Hagiya et al. |
| 2014/0187809 | A1 | 7/2014 | Hori et al. |

FOREIGN PATENT DOCUMENTS

| CN | 101010327 A | 8/2007 |
| CN | 101137601 A | 3/2008 |
| CN | 101796050 A | 8/2010 |
| EP | 2695887 A1 | 2/2014 |
| JP | 2006-522064 A | 9/2006 |
| JP | 2009-502893 A | 1/2009 |
| JP | 2009-510026 A | 3/2009 |
| JP | 2011-511031 A | 4/2011 |
| RU | 2229476 C2 | 5/2004 |
| WO | WO 2004/087168 A1 | 10/2004 |
| WO | WO 2006/106483 A1 | 10/2006 |
| WO | WO 2007/012793 A1 | 2/2007 |
| WO | WO 2007/039563 A1 | 4/2007 |
| WO | WO 2009/006734 A1 | 1/2009 |
| WO | WO 2009/098209 A1 | 8/2009 |
| WO | WO 2010/114137 A1 | 10/2010 |
| WO | WO 2012/137460 A1 | 10/2012 |
| WO | WO 2013/010275 A1 | 1/2013 |

OTHER PUBLICATIONS

International Search Report dated Sep. 22, 2014, in PCT/JP2014/071434.
Edited by CSJ: The Chemical Society of Japan, Jikken Kagaku Koza 20 Yuki Gosei II—Alcohol• Amine-, 4th edition, Maruzen Co., Ltd., Jul. 6, 1992, p. 21.
Office Action dated Aug. 2, 2016, in CN 201480046919.2, with English translation.
Akashi et al., "Catalyst-Controlled Diastereoselection in the Hydrogenation of Heterocycloalkyl Ketones," Adv. Synth. Catal., Aug. 10, 2011, 353:1955-1960.
Office Action dated Dec. 20, 2016, in JP 2015-535403.
Supplementary European Search Report dated Dec. 21, 2016, in EP 14841494.9.
Arai et al., "Asymmetric Hydrogenation of Bicyclic Ketones Catalyzed by BINAP/IPHAN-Ru(II) Complex," Organic Letters, Aug. 6, 2010 (online Jul. 12, 2010), 12(15):3380-3383.
Doucet et al., "Trans-[RuCl$_2$(phosphane)2(1,2-diamine)] and Chiral transgRuCl$_2$(diphosphane)(1,2-diamine): Shelf-Stable Precatalysts for the Rapid, Productive, and Stereoselective Hydrogenation of Ketones," Angewandte Chemie, International Edition, 1998, 37(12):1703-1707.
House et al., "Reduction of Azabicyclic Ketones," The Journal of Organic Chemistry, Sep. 1, 1963, 28:2407-2416.
Matsumura et al., "Chiral Ruthenabicyclic Complexes: Precatalysts for Rapid, Enantioselective, and Wide-Scope Hydrogenation of Ketones," Journal of the American Chemical Society, Jul. 20, 2011 (online Jun. 16, 2011), 133(28):10696-10699.
Ohkuma et al., "Asymmetric Hydrogenation of 2-Arylated Cycloalkanones through Dynamic Kinetic Resolution," Synlett, 2004, 8:1383-1386.

(Continued)

*Primary Examiner* — Noble E Jarrell
*Assistant Examiner* — John S Kenyon
(74) *Attorney, Agent, or Firm* — Foley & Lardner LLP

(57) ABSTRACT

A 9-azabicyclo[3.3.1]nonan-3-one derivative is reacted with a hydrogen in the presence of a catalyst composed of a ruthenium complex to obtain, at a low cost, an endo-9-azabicyclo[3.3.1]nonan-3-ol derivative useful as a production intermediate for agrochemical agents or medicines.

1 Claim, No Drawings

(56) References Cited

OTHER PUBLICATIONS

Decision on grant dated Oct. 19, 2017, in RU 2016106368, with English translation.

METHOD FOR PRODUCING ENDO-9-AZABICYCLO[3.3.1]NONAN-3-OL DERIVATIVE

TECHNICAL FIELD

The present invention relates to a method for producing an endo-9-azabicyclo[3.3.1]nonan-3-ol derivative.

CROSS-REFERENCE TO RELATED APPLICATIONS

The present invention is a National Stage application of PCT/H2014/071434, filed Aug. 14, 2014, which claims priority on the basis of Japanese Patent Application No. 2013-185712 filed in Japan on Sep. 6, 2013, the contents of which are incorporated herein by reference.

BACKGROUND OF THE INVENTION

An endo-9-azabicyclo[3.3.1]nonan-3-ol derivative is a useful compound applicable as an agrochemical or medicinal intermediate (Patent Document 1). Patent Document 1 discloses that endo-9-benzyl-9-azabicyclo[3.3.1]nonan-3-ol is synthesized by reducing 9-benzyl-9-azabicyclo[3.3.1]nonan-3-one in a methanol solvent with sodium borohydride. However, there is no report disclosing study to reduce an azabicyclo nonane compound in the presence of a ruthenium catalyst.

DOCUMENTS OF RELATED ART

Patent Documents

Patent Document 1: Japanese Translation of PCT International Application Publication No. 2009-510026

SUMMARY OF THE INVENTION

Problems to be Solved by the Invention

An object of the present invention is to provide a method for conducting a reaction in which a 9-azabicyclo[3.3.1]nonan-3-one derivative is reduced to obtain the correspondent endo-9-azabicyclo[3.3.1]nonan-3-ol derivative at a low cost by a simplified process.

Means to Solve the Problems

The present invention includes the following aspects.
(1) A method for producing a compound represented by the following formula (II), including reacting a compound represented by the following formula (I) with a hydrogen in the presence of a catalyst composed of a ruthenium complex.

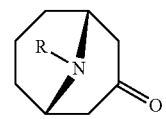

(I)

(II)

In the formulae (I) and (II), R represents a hydrogen atom, an unsubstituted or substituted alkyl group, an unsubstituted or substituted aralkyl group, or an unsubstituted or substituted alkoxycarbonyl group.
(2) The method as described in (1), wherein the ruthenium complex is a compound represented by the following formula: $Ru(X)(Y)(Px)_n(L)$ or $Ru(X)(Y)(PN)_2$.

In the formulae, X and Y each independently represents an anionic ligand.

Px represents a phosphine ligand. n represents 1 or 2.

L represents a ligand represented by the following formula (III) or a diamine ligand.

PN represents a ligand represented by the following formula (IV).

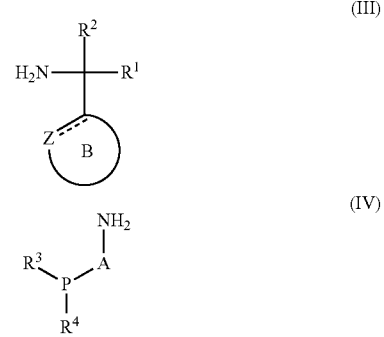

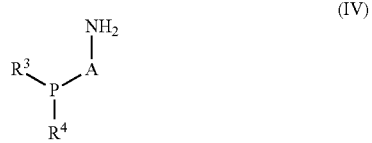

In the formula (III), $R^1$ and $R^2$ each independently represents a hydrogen atom, an unsubstituted or substituted alkyl group, an unsubstituted or substituted aryl group, or an unsubstituted or substituted aralkyl group. The ring B represents an unsubstituted or substituted hetero ring, and a double line portion composed of a continuous line and a dotted line represents a single bond or a double bond, and Z represents a coordinating atom selected from the group consisting of N, P, O, and S.

In the formula (IV), $R^3$ and $R^4$ each independently represents an unsubstituted or substituted alkyl group an unsubstituted or substituted aryl group, or an unsubstituted or substituted aralkyl group. A represents an unsubstituted or substituted C1 to 4 alkylene group.
(3) The method as described in (2), wherein the ruthenium complex is a compound represented by the following formula: $Ru(X)(Y)(Px)_n(L)$, and L represents pyridin-2-yl methanamine, (1-methyl-1H-benzimidazol-2-yl)methanamine, (5-methylpyrazin-2-yl) methanamine, benzoxazol-2-yl methanamine, pyrimidin-2-yl methanamine, thiazol-2-yl methanamine, or (pyrazin-2-yl)methanamine.
(4) The method as described in (2), wherein the ruthenium complex is a compound represented by the following formula: $Ru(X)(Y)(Px)_n(L)$, and L represents a diamine ligand represented by the following formula (VI).

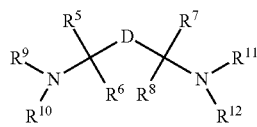

In the formula (VI), $R^5$ to $R^{12}$ each independently represents a hydrogen atom, an unsubstituted or substituted alkyl group, an unsubstituted or substituted aryl group, or an unsubstituted or substituted aralkyl group, two of $R^5$ to $R^{12}$ may be bonded to form a ring, and D represents a single bond, an unsubstituted or substituted alkylene group, an unsubstituted or substituted cycloalkylene group, an unsubstituted or substituted arylene group, or an unsubstituted or substituted divalent hetero ring group.

(5) The method as described in (2), wherein the ruthenium complex is a compound represented by the following formula: $Ru(X)(Y)(PN)_2$, and PN represents a ligand represented by the following formula (V).

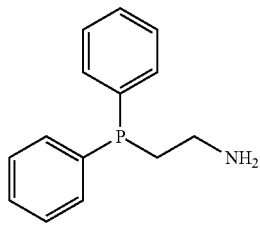

(V)

(6) The method as described in any one of (1) to (5), wherein, in the formulae (I) and (II), R represents an unsubstituted or substituted aralkyl group, and the unsubstituted or substituted aralkyl group is a benzyl group.

Effects of the Invention

In the case where a reaction in which a 9-azabicyclo [3.3.1]nonan-3-one derivative is reduced to an endo-9-azabicyclo[3.3.1]nonan-3-ol derivative is conducted in the presence of a catalyst composed of a ruthenium complex in accordance with the method of the present invention, almost no waste product is generated, extraction of a water-soluble compound is not needed, and the reaction can be conducted at a lower cost in a simplified process compared to a reaction using a boron-based reductant.

EMBODIMENTS FOR CARRYING OUT THE INVENTION

The present invention relates to a method for producing an endo-9-azabicyclo[3.3.1]nonan-3-ol derivative by reacting a 9-azabicyclo[3.3.1]nonan-3-one derivative with a hydrogen in the presence of a catalyst composed of a ruthenium complex.

First, meanings of the terms "unsubstituted" and "substituted" in the present specification will be explained.

The term "unsubstituted" means a group consisting of a mother nucleus. In the case where only a name of a group consisting of a mother nucleus is indicated without describing "substituted", the group means an "unsubstituted" group unless mentioned otherwise.

On the other hand, the term "substituted" means that any of hydrogen atoms in a group forming a mother nucleus is substituted with a group having a structure similar to or different from that of the mother nucleus. Accordingly, a "substituent" is another group bonded to a group forming a mother nucleus. The number of substituents may be one, or two or more. The two or more substituents may be the same or different from each other.

The term "C1 to 6", for example, means that the number of carbon atoms in a group forming a mother nucleus is 1 to 6. The number of carbon atoms does not include the number of carbon atoms present in substituents. For example, a butyl having an ethoxy group as a substituent is classified into a C2 alkoxy C4 alkyl group.

The "substituent" is not particularly limited, provided that the substituent is chemically acceptable and exhibits effects of the present invention. Examples of a group that can be the "substituent" include: halogeno groups such as a fluoro group, a chloro group, a bromo group, and an iodine group; C1 to 8 alkyl groups such as a methyl group, an ethyl group, a n-propyl group, an i-propyl group, a n-butyl group, a s-butyl group, an i-butyl group, a t-butyl group, a n-pentyl group, and a n-hexyl; C3 to 6 cycloalkyl groups such as a cyclopropyl group, a cyclobutyl group, a cyclopentyl group, and a cyclohexyl group; C2 to 6 alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl; C3 to 6 cycloalkenyl groups such as a 2-cyclopropenyl group, a 2-cyclopentenyl group, and 3-cyclohexenyl; C2 to 6 alkynyl groups such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-2-pentynyl group, a 1-hexynyl group, and a 1,1-dimethyl-2-butynyl group;

C1 to 6 alkoxy groups such as a methoxy group, an ethoxy group, a n-propoxy group, an i-propoxy group, a n-butoxy group, a s-butoxy group, an i-butoxy group, and a t-butoxy group; C2 to 6 alkenyloxy groups such as a vinyloxy group, an allyloxy group, a propenyloxy group, and a butenyloxy group; C2 to 6 alkynyloxy groups such as an ethynyloxy group, and a propargyloxy group; C6 to 10 aryl groups such as a phenyl group, and a naphthyl group; C6 to 10 aryloxy groups such as a phenoxy group, and a 1-naphthoxy group; C7 to 11 aralkyl groups such as a benzyl group, and a phenethyl group; C7 to 11 aralkyloxy groups such as a benzyloxy group, and a phenethyloxy group; C1 to 7 acyl groups such as a formyl group, an acetyl group, a propionyl group, a benzoyl group, and a cyclohexylcarbonyl group; C1 to 7 acyloxy groups such as a formyloxy group, an acetyloxy group, a propionyloxy group, a benzoyloxy group, and a cyclohexyl carbonyloxy group; C1 to 6 alkoxycarbonyl groups such as a methoxy carbonyl group, an ethoxycarbonyl group, a n-propoxycarbonyl group, an i-propoxycarbonyl group, a n-butoxycarbonyl group, and a t-butoxycarbonyl group: a carboxyl group;

a hydroxyl group; an oxo group; C1 to 6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group; C2 to 6 haloalkenyl groups such as a 2-chloro-1-propenyl group, and a 2-fluoro-1-butenyl group; C2 to 6 haloalkynyl groups such as a 4,4-dichloro-1-butynyl group, a 4-fluoro-1-pentynyl group, and a 5-bromo-2-pentynyl group; C1 to 6 haloalkoxy groups such as a 2-chloro-n-propoxy group, and a 2,3-dichlorobutoxy group; C2 to 6 haloalkenyloxy groups such as a 2-chloropropenyloxy group, and a 3-bromobutenyloxy group; C6 to 10 haloaryl groups such as a 4-chlorophenyl group, a 4-fluorophenyl group, and a 2,4-dichlorophenyl group; C6 to 10 haloaryloxy groups such as a 4-fluorophenyloxy group, and a 4-chloro-1-naphthoxy group; C1 to 7 haloacyl groups such as a chloroacetyl group, a trifluoroacetyl group, a trichloroacetyl group, and a 4-chlorobenzoyl group; a cyano group; an isocyano group; a nitro group; an isocyanato group; a cyanate group; an azide group;

a mercapto group; an isothiocyanato group; a thiocyanato group; C1 to 6 alkylthio groups such as a methylthio group, an ethylthio group, a n-propylthio group, an i-propylthio group, a n-butylthio group, an i-butylthio group, a s-butylthio group, and a t-butylthio group; C2 to 6 alkenylthio groups such as a vinylthio group, and an allylthio group; C2 to 6 alkynylthio groups such as an ethynylthio group, and a propargylthio group; C6 to 10 arylthio groups such as a phenylthio group, and a naphthylthio group; heteroarylthio groups such as a thiazolylthio group, and a pyridylthio group; C7 to 11 aralkylthio groups such as a benzylthio group, and a phenethylthio group; (C1 to 6 alkylthio) carbonyl groups such as a (methylthio)carbonyl group, an (ethylthio)carbonyl group, a (n-propylthio)carbonyl group, an (i-propylthio)carbonyl group, a (n-butylthio)carbonyl group, an (i-butylthio)carbonyl group, a (s-butylthio)carbonyl group, and a (t-butylthio)carbonyl group;

C1 to 6 alkylsulfinyl groups such as a methylsulfinyl group, an ethylsulfinyl group, and a t-butylsulfinyl group; C2 to 6 alkenylsulfinyl groups such as an allylsulfinyl group; C2 to 6 alkynylsulfinyl groups such as a propargylsulfinyl group; C6 to 10 arylsulfinyl group such as a phenylsulfinyl group; heteroarylsulfinyl groups such as a thiazolylsulfinyl group, and a pyridylsulfinyl group; C7 to 11 aralkylsulfinyl groups such as a benzylsulfinyl group, and a phenethylsulfinyl group; C1 to 6 alkylsulfonyl groups such as a methylsulfonyl group, an ethylsulfonyl group, and a t-butylsulfonyl group; C2 to 6 alkenylsulfonyl groups such as an allylsulfonyl group; C2 to 6 alkynylsulfonyl groups such as a propargylsulfonyl group; C6 to 10 arylsulfonyl groups such as a phenylsulfonyl group; heteroarylsulfonyl groups such as a thiazolylsulfonyl group, and a pyridylsulfonyl group; C7 to 11 aralkylsulfonyl groups such as a benzylsulfonyl group, and a phenethylsulfonyl group;

6-membered heteroaryl groups such as a pyridyl group, a pyrazinyl group, a pyrimidinyl group, a pyridazinyl group, and a triazinyl group; saturated hetero ring groups such as an aziridinyl group, an epoxy group, a pyrrolidinyl group, a tetrahydrofuranyl group, a piperidyl group, a piperazinyl group, and a morpholinyl group; tri C1 to 6 alkylsilyl groups such as a trimethylsilyl group, a triethylsilyl group, and a t-butyldimethylsilyl group; and a triphenylsilyl group.

The "substituent" may further have another "substituent". For example, a butyl group serving as a substituent may have an ethoxy group as another substituent, that is, the substituent may be an ethoxybutyl group.

A 9-azabicyclo[3.3.1]nonan-3-one derivative used as a reaction raw material in the present invention is a compound represented by the following formula (I). In the formula (I), R represents a hydrogen atom, an unsubstituted or substituted alkyl group, an unsubstituted or substituted aralkyl group, or an unsubstituted or substituted alkoxycarbonyl group. Among these, a hydrogen atom, a C1 to 6 alkyl group, a C7 to 11 aralkyl group, a C1 to 6 alkoxycarbonyl group, or the like is preferred, a hydrogen atom, a methyl group, a benzyl group, a t-butoxycarbonyl group, or the like is more preferred, and a hydrogen atom or a benzyl group is even more preferred. The 9-azabicyclo[3.3.1]nonan-3-one derivative, serving as a reaction raw material, may be one purified by various methods. Examples of the purification methods include a recrystallization method, an alkali washing method, and a column method.

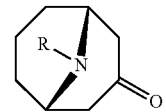

(I)

A ruthenium complex available in the present invention is not particularly limited, provided that the ruthenium complex serves as a catalyst during hydrogenation reaction. The ruthenium complex preferably used in the present invention is a compound represented by the following formula: $Ru(X)(Y)(Px)_n(L)$ or $Ru(X)(Y)(PN)_2$.

In the formulae, X and Y each independently represents an anionic ligand. X and Y may be the same or different from each other. X and Y may be bonded together to form an at least bidentate anionic ligand.

Examples of the anionic ligand include: $CF_3SO_3^-$, $BF_4^-$, $PF_6^-$, $ClO_4^-$; halogeno groups such as a fluoro group, a chloro group, a bromo group, and an iodine group; a hydride group; a hydroxyl group; unsubstituted or substituted diketonate groups such as an acetylacetonate; unsubstituted or substituted cyclopentadienyl groups; unsubstituted or substituted alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; unsubstituted or substituted alkyl groups such as a methyl group, an ethyl group, a n-propyl group, an i-propyl group, a n-butyl group, a s-butyl group, an i-butyl group, a t-butyl group, a n-pentyl group, and a n-hexyl group; unsubstituted or substituted aryl groups such as a phenyl group, and a naphthyl group;

unsubstituted or substituted alkoxy groups such as a methoxy group, an ethoxy group, a n-propoxy group, an i-propoxy group, a n-butoxy group, a s-butoxy group, an i-butoxy group, and a t-butoxy group; unsubstituted or substituted aryloxy groups such as a phenoxy group, and a 1-naphthoxy group; unsubstituted or substituted alkoxycarbonyl groups such as a methoxy carbonyl group, an ethoxy carbonyl group, a n-propoxy carbonyl group, an i-propoxy carbonyl group, a n-butoxy carbonyl group, and a t-butoxy carbonyl group; unsubstituted or substituted carboxyl groups such as a carboxyl group, a methoxy carbonyl group, and an ethoxy carbonyl group; unsubstituted or substituted alkylsulfonate group such as a methylsulfonate group, an ethylsulfonate group, and a t-butylsulfonate group; unsubstituted or substituted arylsulfonate groups such as a phenylsulfonate group; unsubstituted or substituted alkylthio groups such as a methylthio group, an ethylthio group, a n-propylthio group, an i-propylthio group, a n-butylthio group, an i-butylthio group, a s-butylthio group, and a t-butylthio group; unsubstituted or substituted alkenylthio groups such as a vinylthio group, and an allylthio group; unsubstituted or substituted arylthio groups such as a phenylthio group, and a naphthylthio group; unsubstituted or substituted alkylsulfonyl groups such as a methylsulfonyl group, an ethylsulfonyl group, and a t-butylsulfonyl group; and unsubstituted or substituted alkylsulfinyl groups such as a methylsulfinyl group, an ethylsulfinyl group, and a t-butylsulfinyl group. Among these, halogeno groups are preferred.

Px represents a phosphine ligand. n represents 1 or 2. The phosphine ligand is not particularly limited, provided that the phosphine ligand makes it possible to stably form a ruthenium complex. Examples of Px include monodentate phosphine ligands represented by formula (P1) and bidentate phosphine ligands represented by formula (P2).

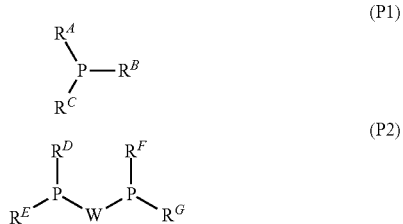

In formula (P1), $R^A$, $R^B$, and $R^C$ each independently represents an unsubstituted or substituted C1 to 20 alkyl group such as a methyl group, an ethyl group, a n-propyl group, an isopropyl group, a n-butyl group, a sec-butyl group, an isobutyl group, a t-butyl group, a pentyl group, a hexyl group, a heptyl group, a nonyl group, or a dodecyl group; an unsubstituted or substituted phenyl group; an unsubstituted or substituted C3 to 8 cycloalkyl group such as a cyclopropyl group, a cyclopentyl group, a cyclohexyl group, or a cyclooctyl group; or an unsubstituted or substituted C7 to 20 aralkyl group such as a benzyl group, an α-methylbenzyl group, or an α,α-dimethylbenzyl group. Two of $R^A$, $R^B$, and $R^C$ may be bonded together to form an unsubstituted or substituted hetero ring. Among these, $R^A$, $R^B$, and $R^C$ preferably represent unsubstituted or substituted phenyl groups.

Examples of the monodentate phosphine ligand represented by formula (P1) that is preferably used in the present invention include tertiary phosphines such as trimethylphosphine, triethylphosphine, tributylphosphine, triphenylphosphine, tricyclohexylphosphine, tri(p-tolyl)phosphine, diphenylmethylphosphine, dimethylphenylphosphine, diisopropylmethylphosphine, 1-[2-(diphenylphosphino)ferrocenyl]ethylmethyl ether, and 2-(diphenylphosphino)-2'-methoxy-1,1'-binaphthyl. In addition, a phosphine ligand in which $R^A$, $R^B$, and $R^C$ represent groups different from each other such as ethylmethylbutylphosphine, ethylmethylphenylphosphine, isopropylethylmethylphosphine, or cyclohexyl(O-anisyl)methylphosphine, may be used.

In formula (P2), $R^D$, $R^E$, $R^F$, and $R^G$ each independently represents an unsubstituted or substituted C1 to 20 alkyl group such as a methyl group, an ethyl group, a n-propyl group, an isopropyl group, a n-butyl group, a sec-butyl group, a t-butyl group, a pentyl group or an isomer thereof, a hexyl group or an isomer thereof, a heptyl group or an isomer thereof, a nonyl group or an isomer thereof, or a dodecyl group or an isomer thereof; an unsubstituted or substituted phenyl group; or an unsubstituted or substituted C3 to 8 cycloalkyl group such as a cyclopropyl group, a cyclopentyl group, or a cyclohexyl group. $R^D$ and $R^E$, and/or, $R^F$ and $R^G$, may be bonded together to form an unsubstituted or substituted hetero ring. Among these, $R^D$, $R^E$, $R^F$, and $R^G$ preferably represent unsubstituted or substituted phenyl groups.

W represents an unsubstituted or substituted C1 to 5 alkylene group such as a methylene group, an ethylene group, a propylene group, a trimethylene group, or a tetramethylene group; an unsubstituted or substituted C3 to 6 cycloalkylene group such as a cyclopropylene group, a cyclobutylene group, a cyclopentylene group, or a cyclohexylene group; an unsubstituted or substituted arylene group such as a phenylene group, a naphthylene group, a 1,1'-biphenyl-2,2'-diyl group, a 1,1'-binaphthyl-2,2'-diyl group, or a 1,1'-binaphthyl-7,7'-diyl group; an unsubstituted or substituted C2 to 20 alkenediyl group such as an ethenediyl group, a propenediyl group, an isopropenediyl group, or a butenediyl group; or an unsubstituted or substituted C2 to 20 alkynediyl group such as an ethynediyl group, or a propynediyl group. Among these, W preferably represents an unsubstituted or substituted C1 to 5 alkylene group or an unsubstituted or substituted arylene group (preferably a 1,1'-biphenyl-2,2'-diyl group, or a 1,1'-binaphthyl-2,2'-diyl group).

Examples of the bidentate phosphine ligand represented by formula (P2) include bisdiphenylphosphino methane, bisdiphenylphosphino ethane, bisdiphenylphosphino propane, bisdiphenylphosphino butane, bisdimethylphosphino ethane, bisdimethylphosphino propane, 1,1'-bis(diphenylphosphino)ferrocene, and 2,2'-bis(diphenylphosphino)-1,1'-biphenyl. Among these, bisdiphenylphosphino butane or 2,2'-bis(diphenylphosphino)-1,1'-biphenyl is preferable.

Additional examples of the preferable bidentate phosphine ligand in the present invention include asymmetric ligands such as 2,2'-bis-(diphenylphosphino)-1,1'-binaphthyl (hereinafter, referred to as BINAP), BINAP derivatives in which a naphthyl ring of BINAP has a substituent such as an alkyl group or an aryl group, BINAP derivatives having a fluorine substituent, and BINAP derivatives in which two benzene rings on a phosphorus atom have 1 to 5 substituents such as an alkyl group or an alkoxy group, respectively. Specific examples thereof include 2,2'-bis-(di-p-tolylphosphino)-1,1'-binaphthyl (Tol-BINAP), 2,2'-bis[bis(3,5-dimethylphenyl)phosphino]-1,1'-binaphthyl (Xylyl-BINAP), 1-[1',2-bis(diphenylphosphino)ferrocenyl]ethyldiamine, 2,2'-bis-(dicyclohexylphosphino)-6,6'-dimethyl-1,1'-biphenyl, 2,3-bis-(diphenylphosphino) butane, 1-cyclohexyl-1,2-bis-(diphenylphosphino)ethane, 1-substituted-3,4-bis-(diphenylphosphino)pyrrolidine, 2,3-O-isopropylidene-2,3-dihydroxy-1,4-bis-(diphenylphosphino)butane, 1,2-bis [(O-methoxyphenyl)phenyl phosphino]ethane, substituted-1,2-bis(phospholano)benzene, 5,6-bis-(diphenylphosphino)-2-norbornene, N,N'-bis-(diphenylphosphino)-N, N'-bis(1-phenylethyl)ethylenediamine, 1,2-bis-(diphenylphosphino) propane, 2,4-bis-(diphenylphosphino)pentane, [(5,6),(5',6')-bis(methylenedioxy)biphenyl-2,2'-diyl]bis (diphenylphosphine), 1,2-bis(t-butylmethylphosphino) ethane, and 2,4-bis-(diphenylphosphino)pentane.

Many phosphine ligands (PX) are known and may be prepared and obtained by known methods. In addition, commercially available ones may be directly used, or may be used after purification, as needed. In the ruthenium complex preferably used in the present invention, Px is a bidentate phosphine ligand.

L represents a ligand represented by the following formula (III) or a diamine ligand.

In formula (III), $R^1$ and $R^2$ each independently represents a hydrogen atom, an unsubstituted or substituted alkyl group, an unsubstituted or substituted aryl group, or an unsubstituted or substituted aralkyl group. Ring B represents an unsubstituted or substituted hetero ring, a double line portion composed of a continuous line and a dotted line represents a single bond or a double bond, and Z represents a coordinating atom selected from the group consisting of N, P, O, and S.

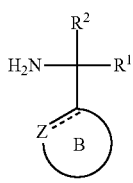

(III)

Examples of an alkyl group include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, a 2,2-dimethylpropyl group, and an i-hexyl group.

Examples of a substituted alkyl group include: C3 to 8 cycloalkyl C1 to 6 alkyl groups such as a cyclopropylmethyl group, a 2-cyclopropylethyl group, a cyclopentylmethyl group, a 2-cyclohexylethyl group, and a 2-cyclooctylethyl group; haloalkyl groups such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, and a 2,4,6-trichlorohexyl group; and alkoxyalkyl groups such as a methoxymethyl group, an ethoxymethyl group, a methoxyethyl group, an ethoxyethyl group, a methoxy-n-propyl group, an ethoxymethyl group, an ethoxyethyl group, a n-propoxymethyl group, an i-propoxyethyl group, a s-butoxymethyl group, and a t-butoxyethyl group.

Examples of an aryl group include a phenyl group, a naphthyl group, an azulenyl group, an indenyl group, an indanyl group, and a tetralinyl group. Preferable examples of a substituent on an aryl group include halogeno groups such as a fluoro group, a chloro group, a bromo group, and an iodine group; alkyl groups such as a methyl group, an ethyl group, a n-propyl group, an i-propyl group, a n-butyl group, a s-butyl group, an i-butyl group, a t-butyl group, a n-pentyl group, and a n-hexyl group; a hydroxyl group; alkoxy groups such as a methoxy group, an ethoxy group, and a n-propyl group; and a cyano group.

Examples of an aralkyl group include a benzyl group, and a phenethyl group. Preferable examples of a substituent on an aralkyl group include halogeno groups such as a fluoro group, a chloro group, a bromo group, and an iodine group; alkyl groups such as a methyl group, an ethyl group, a n-propyl group, an i-propyl group, a n-butyl group, a s-butyl group, an i-butyl group, a t-butyl group, a n-pentyl group, and a n-hexyl group; a hydroxyl group; alkoxy groups such as a methoxy group, an ethoxy group, and a n-propyl group; and a cyano group.

Among these, $R^1$ and $R^2$ preferably represent a hydrogen atom or an unsubstituted or substituted C1 to 6 alkyl group.

Ring B represents an unsubstituted or substituted hetero ring. The ring B has the coordinating atom Z on an atom adjacent to a bonding portion thereon. The coordinating atom Z represents N, P, O, or S.

Examples of an unsubstituted or substituted hetero ring group include unsubstituted or substituted 5-membered heteroaryl groups, unsubstituted or substituted 6-membered heteroaryl groups, unsubstituted or substituted condensed ring heteroaryl groups, unsubstituted or substituted saturated/unsaturated hetero 5-membered ring groups, and unsubstituted or substituted saturated/unsaturated hetero 6-membered ring groups.

Examples of the "unsubstituted or substituted 5-membered heteroaryl groups" include: pyrrolyl groups such as a pyrrol-2-yl group; furyl groups such as a furan-2-yl group; thienyl groups such as a thiophen-2-yl group; imidazolyl groups such as an imidazol-2-yl group, an imidazol-5-yl group, a 1-methylimidazol-2-yl group, and a 1-methylimidazol-4-yl group; pyrazolyl groups such as a pyrazol-3-yl group, and a pyrazol-5-yl group; oxazolyl groups such as an oxazol-2-yl group, an oxazol-4-yl group, and an oxazol-5-yl group; isoxazolyl groups such as an isoxazol-3-yl group, and an isoxazol-5-yl group; thiazolyl groups such as a thiazol-2-yl group; isothiazolyl groups such as an isothiazol-3-yl group, and an isothiazol-5-yl group; triazolyl groups such as a 1,2,3-triazol-4-yl groups, a 1-methyl-1,2,3-triazol-4-yl group, a 1,2,4-triazol-3-yl group, and a 2,3-dimethyl-1,2,4-triazol-5-yl group; oxadiazolyl groups such as a 1,2,3-oxadiazol-4-yl group, a 1,2,3-oxadiazol-5-yl group, and a 1,3,4-oxadiazol-2-yl group; thiadiazolyl groups such as a 1,2,4-thiadiazol-3-yl group, a 1,2,4-thiadiazol-5-yl group, and a 1,3,4-thiadiazol-2-yl group; tetrazolyl groups such as a tetrazol-5-yl group.

Examples of the "unsubstituted or substituted 6-membered heteroaryl group" include: pyridyl groups such as a pyridine-2-yl group; pyrazinyl groups such as a pyrazin-2-yl group, and a 5-methylpyrazin-2-yl group; pyrimidinyl groups such as a pyrimidin-2-yl group, and a pyrimidin-4-yl group, pyridazinyl groups such as a pyridazin-3-yl group, and triazinyl groups such as a 1,3,5-triazin-2-yl group.

Examples of the "unsubstituted or substituted condensed ring heteroaryl group" include: an indol-2-yl group; a benzofuran-2-yl group, a benzothiophen-2-yl group, benzimidazol-2-yl group, a 1-methyl-benzimidazol-2-yl group, a benzoxazol-2-yl group, a benzthiazol-2-yl group, and a quinolin-2-yl group.

Examples of the "unsubstituted or substituted saturated/unsaturated hetero 5-membered ring group" include a pyrrolidin-2-yl group, a tetrahydrofuran-2-yl group, and an oxazolin-2-yl group.

Examples of the "unsubstituted or substituted saturated/unsaturated hetero 6-membered ring group" include a piperidin-2-yl group, a piperazin-2-yl group, and a morpholin-2-yl group.

Among these, the ring B preferably represents an unsubstituted or substituted 5-membered heteroaryl group, an unsubstituted or substituted 6-membered heteroaryl group, or an unsubstituted or substituted condensed ring heteroaryl group, and more preferably represents a thiazolyl group, a pyridyl group, a pyrazinyl group, a pyrimidinyl group, a benzimidazolyl group, or a benzoxazolyl group, that may be substituted with a C1 to 6 alkyl group.

The ligand represented by formula (III) that is preferably used in the present invention is pyridin-2-yl methanamine (see formula (L1)), (1-methyl-1H-benzimidazol-2-yl)methanamine (see formula (L2)), (5-methylpyrazin-2-yl) methanamine (see formula (L3)), benzoxazol-2-yl methanamine (see formula (L4)), pyrimidin-2-yl methanamine (see formula (L5)), or thiazol-2-yl methanamine (see formula (L6)), or (pyrazin-2-yl)methanamine (see formula (L7)).

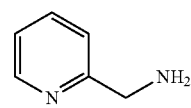

(L1)

-continued

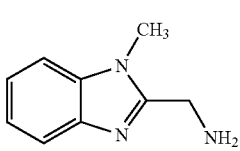 (L2)

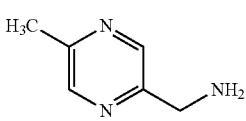 (L3)

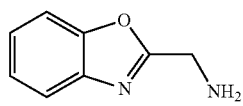 (L4)

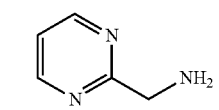 (L5)

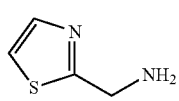 (L6)

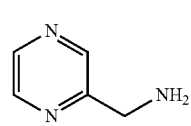 (L7)

The diamine ligand is a compound having two amino groups in a molecule thereof. A diamine ligand represented by formula (VI) is preferably used in the present invention.

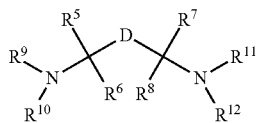 (VI)

In the formula, $R^5$ to $R^{12}$ each independently represents a hydrogen atom, an unsubstituted or substituted alkyl group, an unsubstituted or substituted aryl group, or an unsubstituted or substituted aralkyl group, and two of $R^5$ to $R^{12}$ may be bonded together to form a ring.

Examples of an alkyl group, a substituted alkyl group, an aryl group, a substituted aryl group, an aralkyl group, and a substituted aralkyl group include the same ones mentioned for $R^1$ and $R^2$ in formula (III).

Among these, it is preferable that $R^5$ to $R^{12}$ each independently represents a hydrogen atom, or a C1 to 6 alkyl group.

D represents a single bond, an unsubstituted or substituted alkylene group, an unsubstituted or substituted cycloalkylene group, an unsubstituted or substituted arylene group, or an unsubstituted or substituted divalent hetero ring group.

Examples of an unsubstituted or substituted alkylene group include an ethylene group, a propylene group, a trimethylene group, a tetramethylene group, a pentamethylene group, and a hexamethylene group.

Examples of an unsubstituted or substituted cycloalkylene group include cycloalkylene groups such as a cyclopropylene group, a cyclobutylene group, a cyclopentylene group, a cyclohexylene group, and a bicycloheptenediyl group.

Examples of an unsubstituted or substituted divalent hetero ring group include unsubstituted or substituted (preferably C1 to 6 alkyl-substituted or C1 to 6 alkoxy-substituted) dioxolanyl groups such as a 2,2-dimethyl-1,3-dioxolan-4,5-diyl group, and a 5,6-dimethoxy-5,6-dimethyl-1,4-dioxolan-2,3-diyl group.

Among these, D preferably represents a single bond, or an unsubstituted or substituted divalent hetero ring group, and more preferably represents a single bond, or an unsubstituted or substituted (preferably C1 to 6 alkyl-substituted) dioxolanyl group.

Specific examples of the diamine ligand preferably used in the present invention will be shown below.

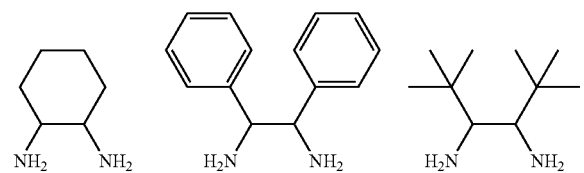

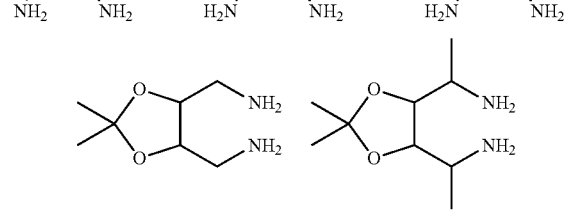

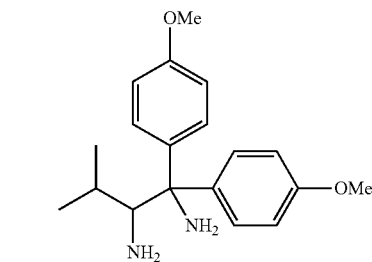

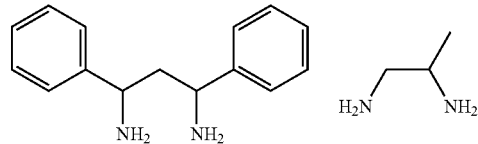

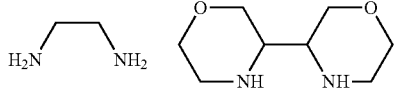

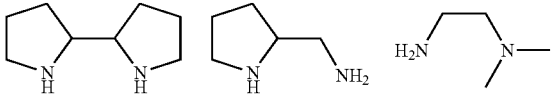

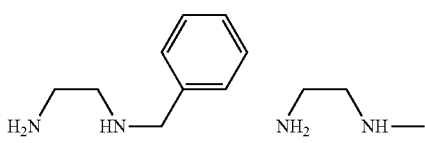

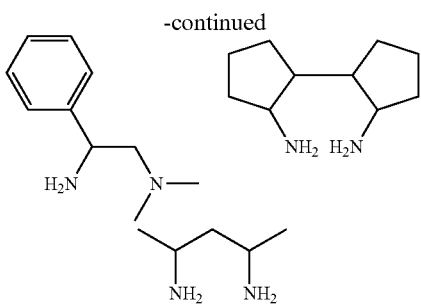

PN represents a ligand represented by the following formula (IV).

In the formula (IV), $R^3$ and $R^4$ each independently represents an unsubstituted or substituted alkyl group, an unsubstituted or substituted aryl group, or an unsubstituted or substituted aralkyl group. A represents an unsubstituted or substituted C1 to 4 alkylene group.

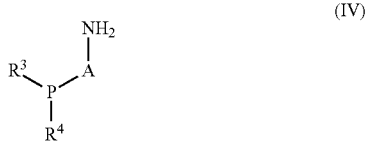

(IV)

Examples of an unsubstituted or substituted alkyl group, an unsubstituted or substituted aryl group, or an unsubstituted or substituted aralkyl group for $R^3$ and $R^4$ include the same ones mentioned for $R^1$ and $R^2$.

Among these, $R^3$ and $R^4$ preferably represent an unsubstituted or substituted alkyl group, or an unsubstituted or substituted aryl group, and more preferably represent a C1 to 6 alkyl group, or a phenyl group.

Examples of an alkylene group include C1 to 4 alkylene groups such as a methylene group, an ethylene group, a propylene group, a trimethylene group, and a tetramethylene group. Preferable examples of a substituent on an alkylene group include: halogeno groups such as a fluoro group, a chloro group, a bromo group, and an iodine group; a hydroxyl group, and a cyano group.

The ruthenium complex preferably used in the present invention is a ligand represented by the following formula (V).

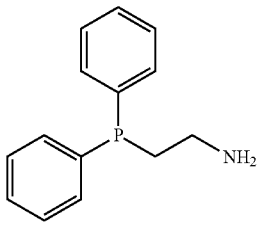

(V)

The ruthenium complex used in the present invention may be prepared by reacting an elemental ruthenium or a ruthenium complex with a desired ligand. The central ruthenium element may be non-valent, monovalent, divalent, trivalent, or higher-valent. It is preferable in the present invention that the divalent ruthenium halide complex be reacted with a desired ligand.

It is preferable in the production method according to the present invention that 0.001 to 10 parts by mole, more preferably 0.01 to 1 parts by mole, of a ruthenium complex be present relative to 100 parts by mole of a 9-azabicyclo[3.3.1]nonan-3-one derivative. In the case where the amount of the ruthenium complex is an excessively low amount, catalyst effects are small, and the reactivity and the selectivity become low. In contrast, in the case where the ruthenium complex is used in an amount more than needed, the production cost becomes high.

A base may be present in the production method according to the present invention. In the case where a ruthenium complex in which a hydride is not coordinated is used as a catalyst, it is preferable that a base be present therein. Examples of the base include: alkali metal hydroxides such as a potassium hydroxide, and a sodium hydroxide; organic bases such as a potassium t-butoxide, a sodium ethoxide, a sodium acetate, and an amine (preferably alkali metal alkoxide); and basic ionic exchange resins. It is preferable that an amount of the base used be 0.002 to 20 parts by mole, more preferably 0.02 to 10 parts by mole, relative to 100 parts by mole of a 9-azabicyclo[3.3.1]nonan-3-one derivative.

A hydrogen gas is generally used as a hydrogen. Known substances that can provide hydrogen may also be used. Examples of the substances that can provide hydrogen include: ones containing a metal such as iron or aluminum, as the main component thereof, and ones containing a metal hydride compound such as a magnesium hydride or a calcium hydride, as the main component thereof.

Although the hydrogen pressure (gauge pressure) during reduction reaction is not particularly limited, the hydrogen pressure is preferably atmospheric pressure to 100 atm. Although the temperature during reduction reaction is not particularly limited, the temperature is preferably 0 to 100° C. The reduction reaction may be conducted in the absence of solvent or in a solvent. The solvent is not particularly limited, provided that the solvent is inactive in reduction reaction. Examples of the solvent include: alcohols such as a methanol, an ethanol, an i-propanol, a n-butanol, a t-butanol, and a cyclohexanol; aromatic series such as a toluene, and a xylene; an N,N-dimethylacetamide, a chloroform, a dichloromethane, a tetrahydrofuran, a 1,2-dimethoxy ethane, and a cyclopentylmethyl ether. It is preferable that an amount of the solvent used be 10 to 10000 parts by mole, more preferably 50 to 2000 parts by mole, relative to 100 parts by mole of a 9-azabicyclo[3.3.1]nonan-3-one derivative.

A 9-azabicyclo[3.3.1]nonan-3-ol derivative, which is a reaction product obtained according to the present invention, is a compound represented by the following formula (II). In formula (II), R represents a hydrogen atom, an unsubstituted or substituted alkyl group, an unsubstituted or substituted aralkyl group, or unsubstituted or substituted alkoxycarbonyl group. Among these, a hydrogen atom, a C1 to 6 alkyl group, a C7 to 11 aralkyl group, or a C1 to 6 alkoxycarbonyl group is preferable, a hydrogen atom, a methyl group, a benzyl group, or a t-butoxycarbonyl group is more preferable, and a hydrogen atom, or a benzyl group is even more preferable. The 9-azabicyclo[3.3.1]nonan-3-ol derivative includes two kinds of isomers composed of an exo isomer and an endo isomer due to the difference of configuration of a hydroxyl group. An endo isomer tends to be selectively obtained by the method according to the present invention. The reaction product obtained by the production method according to the present invention may be purified by a known method.

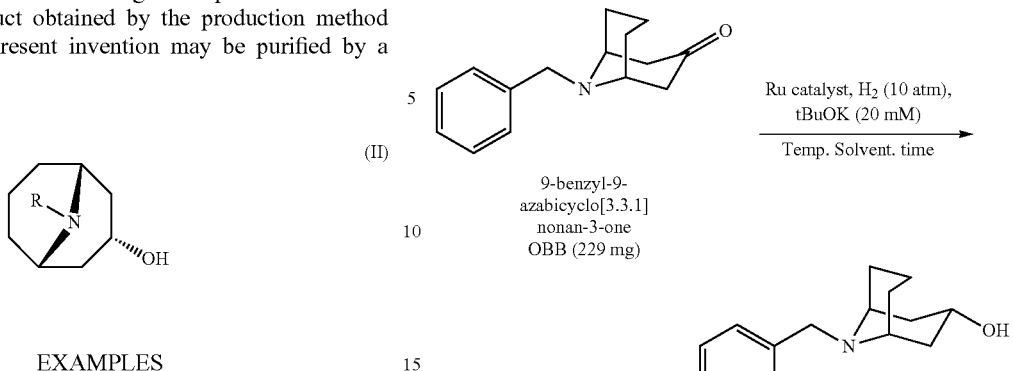

(II)

EXAMPLES

Next, the present invention will be described in more detail based on a series of examples. However, the present invention is in no way limited by these examples.

Example 1

229 mg of a 9-benzyl-9-azabicyclo[3.3.1]nonan-3-one (hereinafter, may be abbreviated as OBB) was dissolved in a solution composed of a solvent shown in Tables 1 and 2, a catalyst composed of a ruthenium complex, and 20 mM of potassium t-butoxide. The temperature of the solution was kept at 25° C., a hydrogen gas at 10 atm (gauge pressure) was injected into the solution, and the reduction reaction was conducted to obtain an endo-9-benzyl-9-azabicyclo[3.3.1]nonan-3-ol (hereinafter, may be abbreviated as endo-HOBB). The results are shown in Tables 1 and 2.

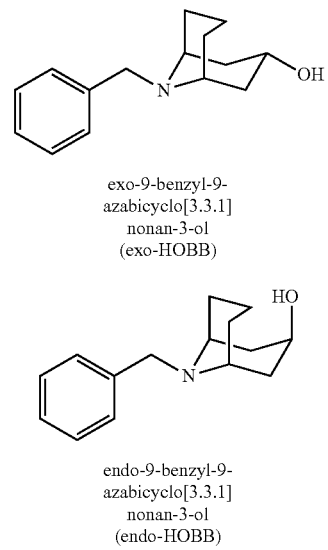

TABLE 1

| No. | Ru catalyst | Subsrate/ Ru catalyst | Solvent | Subsrate concentration (M) | Reactoin time (hour) | Yield (% by area) Target product | Raw materials | endo:exo ratio |
|---|---|---|---|---|---|---|---|---|
| 1 | RuCl$_2$(PPh$_3$)$_2$(en) | 200 | IPA | 1 | 16 | 94 | 4 | 98:2 |
| 2 | RuCl$_2$(PPh$_3$)$_2$(en) | 200 | IPA/toluene (1:1) | 1 | 16 | 84 | 13 | 98:2 |
| 3 | RuCl$_2$(PPh$_3$)$_2$(en) | 200 | IPA/DMA (1:1) | 1 | 16 | 81 | 16 | 98:2 |
| 4 | RuCl$_2$(biphep)(en) | 200 | IPA | 1 | 16 | 2 | 97 | 98:2 |
| 5 | RuCl$_2$(PPh$_3$)$_2$(dmen) | 200 | IPA | 1 | 16 | 12 | 87 | 91:9 |
| 6 | RuCl$_2$(PPh$_3$)$_2$(en) | 200 | IPA/t-BuOH (3:1) | 1 | 64 | 93 | 5 | 98:2 |
| 7* | RuCl$_2$(PPh$_3$)$_2$(en) | 200 | IPA | 1 | 16 | 88 | 11 | 96:4 |
| 8 | trans-RuCl$_2$(PPh$_3$)$_2$(pica) | 200 | IPA | 1 | 64 | 98 | 1 | 95:5 |
| 9 | cis-RuCl$_2$(PPh$_3$)$_2$(pica) | 200 | IPA | 1 | 64 | 98 | 1 | 89:11 |
| 10 | Rucy ™ | 200 | IPA | 0.5 | 2 | 96 | 4 | 99.8:0.2 |
| 11 | Rucy ™ | 1000 | IPA | 0.5 | 16 | 89 | 11 | 99.4:0.6 |
| 12 | Rucy ™ | 1000 | IPA/toluene (1:1) | 1 | 16 | 66 | 34 | 98.9:1.1 |
| 13 | Rucy ™ | 1000 | IPA/ethanol (1:1) | 1 | 16 | 99 | 16 | 99.4:0.6 |

TABLE 2

| No. | Ru catalyst | Subsrate/ Ru catalyst | Solvent | Subsrate concentration (M) | Reation time (hour) | Yield (% by area) Target product | Raw materials | endo:exo ratio |
|---|---|---|---|---|---|---|---|---|
| 14 | RuCl$_2$[(S)-binap][(R)-iphan] | 200 | IPA | 1 | 64 | 99.6 | 0 | 99:1 |
| 15 | RuCl$_2$[biphep][(S)-ipban] | 200 | IPA | 1 | 16 | 99 | 1 | 98:2 |
| 16 | RuCl$_2$[(S)-binap][(R)-dmapen] | 200 | IPA | 1 | 16 | 88 | 12 | 95:5 |

TABLE 2-continued

| No. | Ru catalyst | Subsrate/ Ru catalyst | Solvent | Subsrate concentration (M) | Reation time (hour) | Target product | Raw materials | endo:exo ratio |
|---|---|---|---|---|---|---|---|---|
| 17 | RuCl$_2$(Ph$_2$PCH$_2$CH$_2$NH$_2$)$_2$ | 200 | IPA | 1 | 3 | 99 | 1 | 96:4 |
| 18 | RuCl$_2$(tBu$_2$PCH$_2$CH$_2$NH$_2$)$_2$ | 200 | IPA | 1 | 3 | 5 | 95 | 63:37 |
| 19 | RuCl$_2$(Ph$_2$PCH$_2$CH$_2$CH$_2$NH$_2$)$_2$ | 200 | IPA | 1 | 3 | 93 | 7 | 98:2 |
| 20 | RuCl$_2$[biphep][pica] | 200 | IPA | 1 | 3 | 99 | 1 | 98:2 |
| 21 | RuCl$_2$[biphep][aep] | 200 | IPA | 1 | 3 | 99 | 1 | 96:4 |
| 22 | trans-RuCl$_2$[biphep][ammp] | 200 | IPA | 1 | 3 | 99 | 1 | 99:1 |
| 23 | RuCl$_2$[dppb][ampm] | 200 | IPA | 1 | 3 | 99 | 1 | 98:2 |
| 24 | RuCl$_2$(dppb)(ambo) | 200 | IPA | 1 | 3 | 58 | 42 | 96:4 |
| 25 | RuCl$_2$(dppb)(amtz) | 200 | IPA | 1 | 3 | 99 | 1 | 85:15 |

Abbreviated terms used in the tables are shown below.
* The reaction in No. 7 was conducted while keeping the temperature at 50° C.

PPh$_3$: triphenylphosphine
en: ethylenediamine
IPA: isopropanol
DMA: N,N-dimethylacetamide
biphep: 2,2'-bis-(diphenylphosphino)-1,1'-biphenyl
dmem: N,N-dimethylethylenediamine
pica: α-picolylamine (see formula (L1))
Rucy™: complex represented by formula (c) (manufactured by Takasago International Corporation)

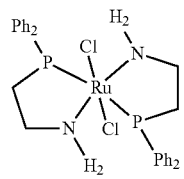

RuCl$_2$(Ph$_2$PCH$_2$CH$_2$NH$_2$)$_2$

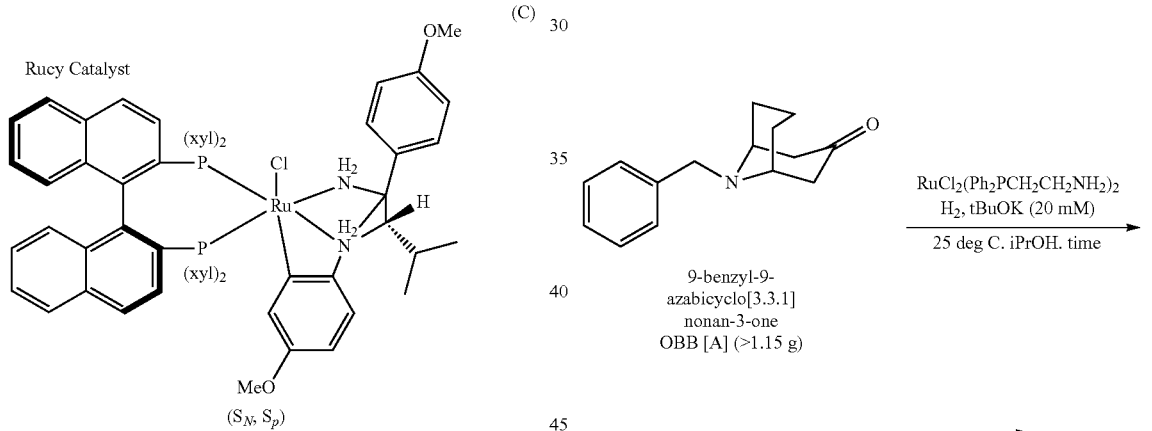

(C)

Rucy Catalyst ($S_N$, $S_p$)

binap: 2,2'-bis-(diphenylphosphino)-1,1'-binaphthyl
(R)-iphan: (2R,3R,4R,5R)-3,4-O-isopropylidenehexane-2,5-diamine
(S)-ipban: (2S,3S)-2,3-O-isopropylidenebutane-1,4-diamine
dmapen: 2-dimethylamino-1-phenylethylamine
aep: 2-(pyridin-2-yl)ethylamine
ammp: (5-methylpyrazin-2-yl) methanamine (see formula (L3))
ampm: pyrimidin-2-yl methanamine (see formula (L5))
ambo: benzoxazol-2-yl methanamine (see formula (L4))
amtz: thiazol-2-yl methanamine (see formula (L6))
dppb: 1,4-bis(diphenylphosphino)butane Example 2

A reduction reaction of a 9-benzyl-9-azabicyclo[3.3.1]nonan-3-one was conducted using RuCl$_2$(Ph$_2$PCH$_2$CH$_2$NH$_2$)$_2$ (manufactured by KANATA Ltd.) under the conditions shown in Table 3. The results are shown in Table 3.

9-benzyl-9-azabicyclo[3.3.1]nonan-3-one
OBB [A] (>1.15 g)

RuCl$_2$(Ph$_2$PCH$_2$CH$_2$NH$_2$)$_2$
H$_2$, tBuOK (20 mM)
—————————————→
25 deg C. iPrOH. time

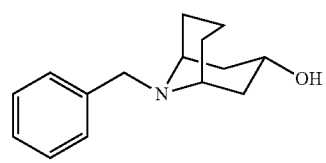

exo-9-benzyl-9-azabicyclo[3.3.1]nonan-3-ol
(exo-HOBB)

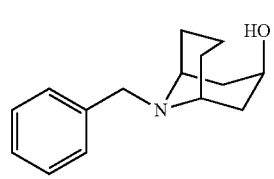

endo-9-benzyl-9-azabicyclo[3.3.1]nonan-3-ol
(endo-HOBB)

TABLE 3

| No. | Catalyst | Hydrogen pressure (atm) | Subsrate/ Ru catalyst | Solvent | Subsrate concentration (M) | Reation time (hour) | Yield (% by area) | | endo:exo ratio |
| --- | --- | --- | --- | --- | --- | --- | --- | --- | --- |
| | | | | | | | Target product | Raw materials | |
| 26 | RuCl$_2$(Ph$_2$PCH$_2$CH$_2$NH$_2$)$_2$ | 10 | 1000 | IPA | 1 | 16 | 98 | 2 | 96.8:3.2 |
| 27 | RuCl$_2$(Ph$_2$PCH$_2$CH$_2$NH$_2$)$_2$ | 50 | 2000 | IPA | 1 | 17 | 99.6 | 0.4 | 97.9:2.1 |
| 28 | RuCl$_2$(Ph$_2$PCH$_2$CH$_2$NH$_2$)$_2$ | 50 | 5000 | IPA | 1 | 18 | 99.7 | 0.3 | 98.4:1.6 |

Example 3

A reduction reaction of OBB was conducted using RuCl$_2$[(S)-binap] [(R)-iphan] under conditions in which the substrate/ruthenium catalyst ratio (S/C) was 1000, and the hydrogen pressure was 50 atm., at room temperature, for 16 hours. The reaction was almost completed, the yield was 99.7%, and the selectivity of endo:exo=99.3:0.7 was obtained.

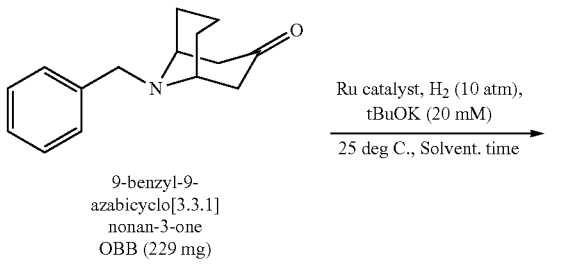

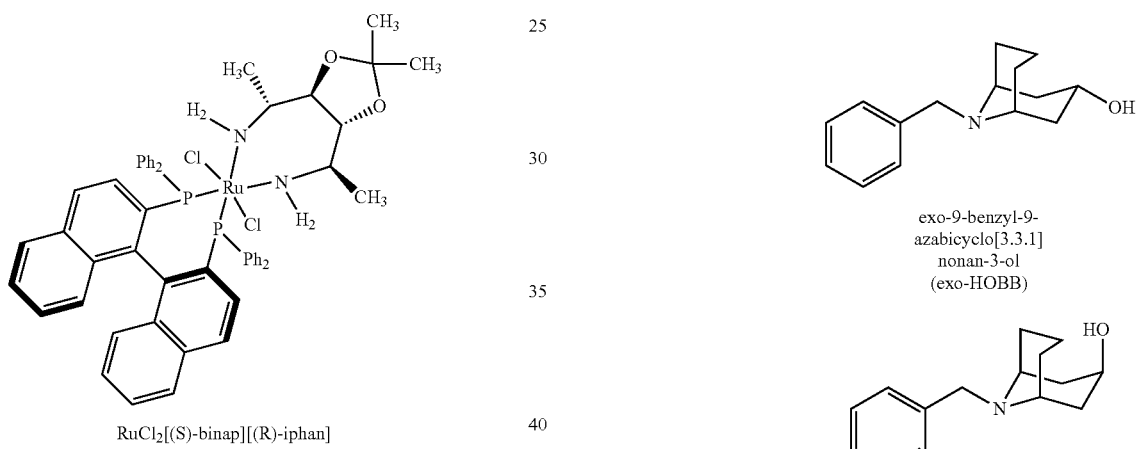

RuCl$_2$[(S)-binap][(R)-iphan]

Example 4

A reduction reaction of a 9-benzyl-9-azabicyclo[3.3.1]nonan-3-one was conducted under the conditions shown in Table 4. The results are shown in Table 4.

TABLE 4

| No. | Catalyst | Subsrate/ Ru catalyst | Solvent | Subsrate concentration (M) | Reation time (hour) | Yield (% by area) | | endo:exo ratio |
| --- | --- | --- | --- | --- | --- | --- | --- | --- |
| | | | | | | Target product | Raw materials | |
| 29 | trans-RuCl$_2$[dppb][ammp] | 200 | IPA | 1 | 3 | 93 | 7 | 70:30 |
| 30 | trans-RuCl$_2$[dppb][ammp] | 200 | ethanol | 1 | 3 | 99 | 1 | 98:2 |
| 31 | trans-RuCl$_2$[dppb][ammp] | 200 | n-butanol | 1 | 3 | 99 | 1 | 97:3 |
| 32 | trans-RuCl$_2$[dppb][ammp] | 1000 | n-butanol | 1 | 3 | 76 | 24 | 98:2 |
| 33 | trans-RuCl$_2$[dppb][ammp] | 1000 | ethanol | 1 | 3 | 97 | 3 | 98.6:1.4 |
| 34 | trans-RuCl$_2$[dppb][ammp] | 5000 | ethanol | 1 | 19 | 99 | 1 | 98.5:1.5 |
| 35 | cis-RuCl$_2$[dppb][ammp] | 1000 | ethanol | 1 | 3 | 99 | 1 | 98.6:1.4 |
| 36 | cis-RuCl$_2$[dppb][ammp] | 10000 | ethanol | 1 | 19 | 98 | 2 | 98.5:1.5 |

Abbreviated terms used in the table are shown below.

ammp: (5-methylpyrazin-2-yl) methanamine (see formula (L3))

dppb: 1,4-bis(diphenylphosphino)butane

Example 5

A reduction reaction of a 9-benzyl-9-azabicyclo[3.3.1]nonan-3-one was conducted using a cis-RuCl$_2$[dppb][Me-bima] under the conditions shown in Table 5. The results are shown in Table 5.

TABLE 5

| No. | Catalyst | Subsrate/Ru catalyst | Solvent | Subsrate concentration (M) | Reation time (hour) | Yield (% by area) Target product | Raw materials | endo:exo ratio |
|---|---|---|---|---|---|---|---|---|
| 37 | cis-RuCl$_2$[dppb][Me-bima] | 200 | methanol | 1 | 3 | 2 | 98 | 98:2 |
| 38 | cis-RuCl$_2$[dppb][Me-bima] | 200 | ethanol | 1 | 3 | 99 | 1 | 99.1:0.9 |
| 39 | cis-RuCl$_2$[dppb][Me-bima] | 200 | IPA | 1 | 3 | 99 | 1 | 78:22 |
| 40 | cis-RuCl$_2$[dppb][Me-bima] | 200 | n-butanol | 1 | 3 | 99 | 1 | 99:1 |
| 41 | cis-RuCl$_2$[dppb][Me-bima] | 200 | toluene | 1 | 3 | 96 | 4 | 50:50 |
| 42 | cis-RuCl$_2$[dppb][Me-bima] | 5000 | n-butanol | 1 | 19 | 99 | 1 | 99:1 |
| 43 | cis-RuCl$_2$[dppb][Me-bima] | 10000 | n-butanol | 1 | 19 | 96 | 4 | 99:1 |

Abbreviated terms used in the table are shown below.

Me-bima: (1-methyl-1H-benzimidazol-2-yl)methanamine (see formula (L2))

dppb: 1,4-bis(diphenylphosphino)butane

Example 6

(Preparation Examples of endo-9-azabicyclo[3.3.1]nonan-3-ol)

A reduction reaction of a 9-azabicyclo[3.3.1]nonan-3-one was conducted using a cis-RuCl$_2$(dppb)(ammp) or a cis-RuCl$_2$(Me-bima) under the conditions shown in Table 6. The results are shown in Table 6.

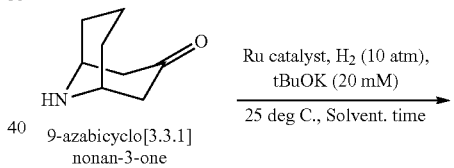
9-azabicyclo[3.3.1]nonan-3-one

Ru catalyst, H$_2$ (10 atm), tBuOK (20 mM)
25 deg C., Solvent. time

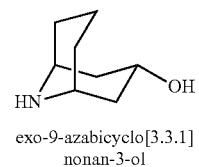
exo-9-azabicyclo[3.3.1]nonan-3-ol

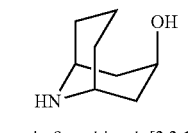
endo-9-azabicyclo[3.3.1]nonan-3-ol

TABLE 6

| No. | Catalyst | Subsrate/Ru catalyst | Solvent | Subsrate concentration (M) | Reactoin time (hour) | Yield (% by area) Target product | endo:exo ratio |
|---|---|---|---|---|---|---|---|
| 44 | cis-RuCl$_2$(dppb)(ammp) | 1000 | ethanol | 1 | 3 | 99 | 96.5:3.5 |
| 45 | cis-RuCl$_2$[dppb][Me-bima] | 1000 | n-butanol | 1 | 3 | 99 | >99:1 |
| 46 | cis-RuCl$_2$[dppb][Me-bima] | 5000 | n-butanol | 1 | 17 | 99 | >99:1 |
| 47 | cis-RuCl$_2$[dppb][Me-bima] | 10000 | n-butanol | 1 | 17 | 99 | >99:1 |

Abbreviated terms used in the table are shown below.

ammp: 2-aminomethyl-5-methylpyrazine (see formula (L3))

Me-bima: (1-methyl-1H-benzimidazol-2-yl)methanamine (see formula (L2))

dppb: 1,4-bis(diphenylphosphino)butane

Example 7

229 mg of OBB was dissolved in a solution composed of an ethanol solvent, a RuCl$_2$(dppb)(ampz) catalyst, and 20 mM of potassium t-butoxide. The catalyst was used so that the substrate/catalyst ratio became 1000. The term "ampz" means (pyrazin-2-yl)methanamine (see formula (L7)).

The temperature of the solution was kept at 30° C., a hydrogen gas at 10 atm. (gauge pressure) was injected into the solution, and the reduction reaction was conducted for 3 hours. 94.5% of HOBB was yielded, and 5.5% of the raw materials were remained. The exo/endo ratio in the resultants were 1.8/98.2.

INDUSTRIAL APPLICABILITY

An endo-9-azabicyclo[3.3.1]nonan-3-ol derivative, useful as a production intermediate for agrochemical agents such as miticides or medicines, is selectively provided at a low cost by reacting a 9-azabicyclo[3.3.1]nonan-3-one derivative with a hydrogen in the presence of a catalyst composed of a ruthenium complex.

The invention claimed is:

1. A method for producing a compound represented by formula (II), comprising reacting a compound represented by formula (I) with a hydrogen in a presence of a catalyst consisting of a ruthenium complex:

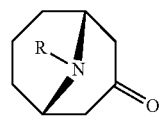
(I)

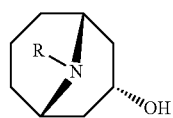
(II)

in the formulae (I) and (II), R represents a benzyl group, and the ruthenium complex is selected from the group consisting of a RuCl$_2$ (PPh$_3$)$_2$(ethylenediamine), a RuCl$_2$ (2,2'-bis-(diphenylphosphino)-1,1'-biphenyl)(ethylenediamine), a RuCl$_2$ (PPh$_3$)$_2$ (N,N-dimethylethylenediamine), a trans-RuCl$_2$(PPh3)$_2$ (α-picolylamine), a cis-RuCl$_2$ (PPh$_3$)$_2$ (α-picolylamine), a rucy catalyst represented by a formula (c):

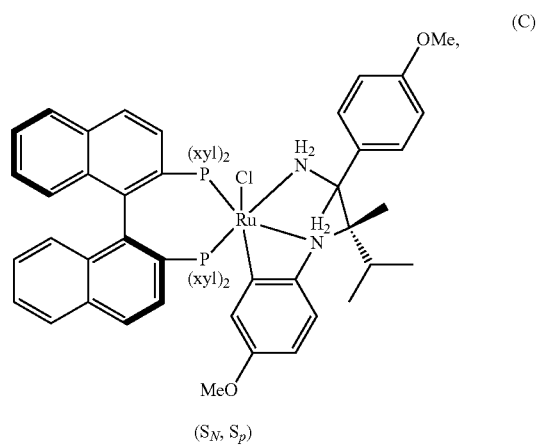
(C)

($S_N$, $S_p$)

a RuCl2 [(S)-2,2'-bis-(diphenylphosphino)-1,1'-binaphthyl] [(2R,3R,4R,5R)-3,4-O-isopropylidenehexane-2,5-diamine], a RuCl$_2$ [2,2'-bis-(diphenylphosphino)-1,1'-biphenyl] [(2S, 3S)-2,3-O-isopropylidenebutane-1,4-diamine], a RuCl$_2$ [(S)-2,2'-bis-(diphenylphosphino)-1,1'-binaphthyl] [(R)-2-dimethylamino-1-phenylethylamine], a RuCl$_2$ (Ph$_2$PCH$_2$CH$_2$NH$_2$)$_2$, a RuCl$_2$ (tBu$_2$PCH$_2$CH$_2$NH$_2$)$_2$, a RuCl$_2$ (Ph$_2$PCH$_2$CH$_2$CH$_2$NH$_2$)$_2$, a RuCl$_2$ [2,2'-bis-(diphenylphosphino)-1,1'-biphenyl] [α-picolylamine], a RuCl$_2$ [2,2'-bis-(diphenylphosphino)-1,1'-biphenyl] [2-(pyridin-2-yl)ethylamine], a trans-RuCl$_2$ [2,2'-bis-(diphenylphosphino)-1,1'-biphenyl] [(5-methylpyrazin-2-yl)methanamine], a RuCl$_2$ [1,4bis(diphenylphosphino)butane] [pyrimidin-2-yl methanamine], a RuCl$_2$ (1,4-bis(diphenylphosphino)butane) (benzoxazol-2-yl methanamine), a RuCl$_2$ (1,4-bis(diphenylphosphino)butane)(thiazol-2-yl methanamine), a trans-RuCl$_2$ [1,4-bis(diphenylphosphino)butane] [(5-methylpyrazin-2-yl) methanamine], a cis-RuCl$_2$ [1,4-bis(diphenylphosphino)butane] [(5-methylpyrazin-2-yl) methanamine], and a cis-RuCl$_2$ [1,4-bis(diphenylphosphino)butane] [(1-methyl-1H-benzimidazol-2-yl)methanamine].

* * * * *